United States Patent [19]

Molinari

[11] Patent Number: 5,112,978
[45] Date of Patent: May 12, 1992

[54] PROCESS FOR PREPARING ALPHA (ALKYL PHENYL)-4(HYDROXY-DIPHENYLMETHYL)-1-PIPERIDINYL BUTANOL

[75] Inventor: Egidio Molinari, Longoneal Segrino, Italy

[73] Assignee: Erregierre Industria Chimica S.p.A., Italy

[21] Appl. No.: 411,021

[22] Filed: Sep. 22, 1989

Related U.S. Application Data

[63] Continuation-in-part of Ser. No. 188,919, May 2, 1988, abandoned.

[30] Foreign Application Priority Data

May 26, 1987 [IT] Italy ................. 20674 A/87

[51] Int. Cl.$^5$ .......................................... C07D 211/22
[52] U.S. Cl. ..................................... 546/240; 346/241
[58] Field of Search ................................ 546/240, 241

[56] References Cited

U.S. PATENT DOCUMENTS 4,673,683 6/1987 Buschmann et al. ............. 546/240

FOREIGN PATENT DOCUMENTS 547193 5/1986 Spain .

OTHER PUBLICATIONS

*Chemical Abstracts*, 107:23250y Abstract of Spanish Patent ES 522, 610, published Sep. 16, 1984 (1987).

*Primary Examiner*—C. Warren Ivy
*Assistant Examiner*—Ba K. Trinh
*Attorney, Agent, or Firm*—Parkhurst, Wendel & Rossi

[57] ABSTRACT

A process for preparing alpha-(alkylphenyl)-4-(hydroxy diphenylmethyl)-1-piperidine butanols of formula (I)

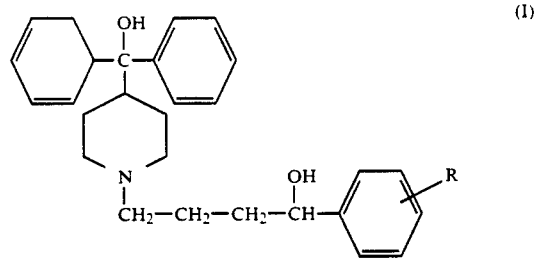

in which R is a $C_1$–$C_5$ alkyl, by reacting an isonipecotate of formula (II):

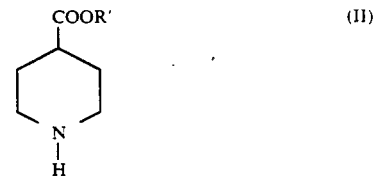

in which R' is a $C_1$–$C_5$ alkyl or benzyl, with 1-(alkylphenyl)-4-chlorobutanol to obtain the compound (IV) directly

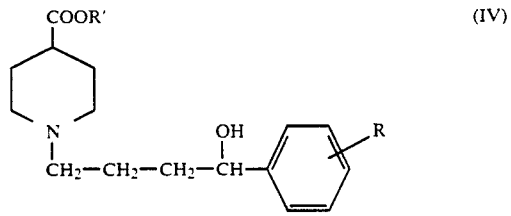

and reacting (IV) with phenylmagnesium halide (V) to obtain (I).

9 Claims, No Drawings

PROCESS FOR PREPARING ALPHA (ALKYL PHENYL)-4(HYDROXY-DIPHENYLMETHYL)-1-PIPERIDINYL BUTANOL

This is a continuation-in-part of application Ser. No. 07/188,919, filed on May 2, 1988, now abandoned.

This invention relates to a new process for preparing alpha-(alkyl phenyl)-4-(hydroxy di phenyl methyl)-1-piperidinyl butanol of formula (I).

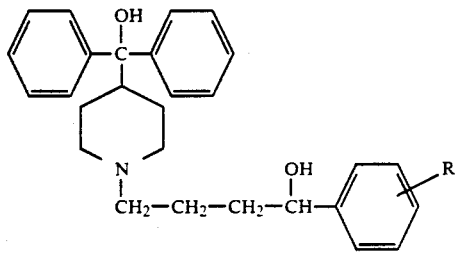

in which R is a $C_1$-$C_5$ alkyl radical.

The process according to the present invention is particularly useful for preparing alpha-(alkyl phenyl)-4-(hydroxy diphenyl methyl)-1-piperidinyl butanol, known as terfenadine, an important pharmaceutical principle demonstrating antihistaminic activity.

Processes for preparing terfenadine are known. J. Castaner in "Drugs of the future" vol III, No. 3, 1978 describes processes starting from azacyclonol or alpha-diphenyl-4-piperidine methanol which is a very costly compound.

ES 522610 describes a process for preparing terfenadine and comprising the following steps:

a) reacting alkyl isonipecotate of formula II

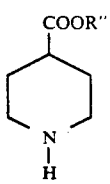

wherein R" is a $C_1$-$C_4$ alkyl radical; with 4-chloro or 4-bromo-1-(terbutyl phenyl)1 butanone of formula III:

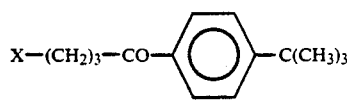

with alkaline carbonates or bicarbonates in the presence of small quantities of KI as the catalyst, and of solvents selected from benzene, dioxane, toluene or polar solvents such as dimethylformamide or dimethylsulfoxide to obtain the compound of formula IV:

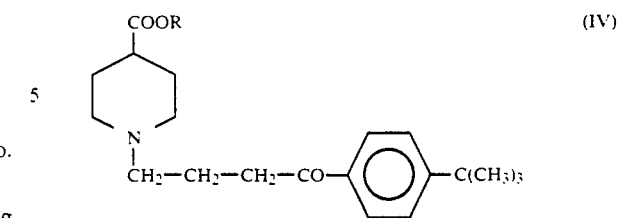

b) reducing the ketonic group of the compound of formula IV with $NaBH_4$ by using as the solvent methanol or ethanol to obtain the compound of formula V

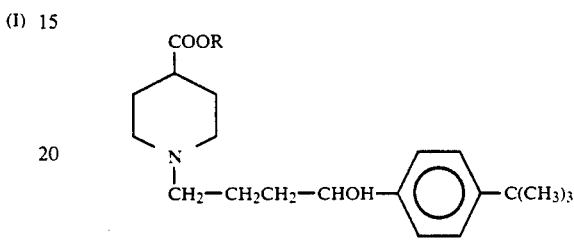

c) reacting the compound of formula V with phenyl magnesium bromide to obtain the terfenadine.

This process has the disadvantage that the yields in the final products the terfenadine are rather low (24%), furthermore the reducing step (b) requires selective conditions in order to avoid the reduction of the ester substituent present on the piperidinic ring such as operating at low temperatures in the presence of anhydrous solvents.

ES 547193 describes a process for preparing the terfenadine involving the following steps:

a) protecting the carbonyl group of the compound 4-chloro or 4-bromo-1-(terbutyl phenyl)1 butanone of formula III with ethylene glycol to obtain 2-(3chloro propyl)-2-[4-(1,1-dimethyl)phenyl]-1,3-dioxolane of formula VI:

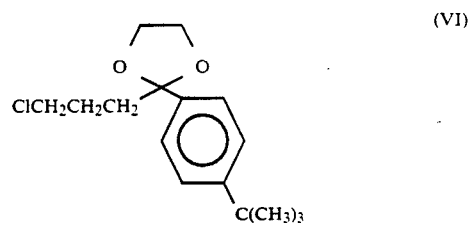

b) reacting the compound of formula (VI) with alkyl isonipecotate of formula II above mentioned with anhydrous potassium carbonate under phase transfer conditions, to obtain the compound of formula (VII):

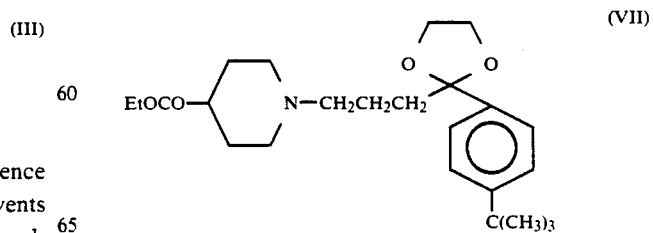

c) reacting the compound VII with phenyl magnesium bromide eliminating the carbonylic protecting group with chlorhydric acid to obtain the compound VIII:

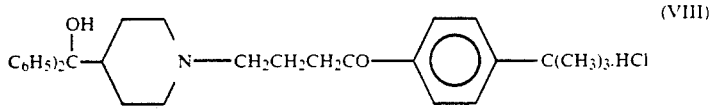

d) reducing the ketonic group in the compound of formula (VIII) with sodium borohydride to obtain the terfenadine of formula (I).

This process requires a considerable number of steps and furthermore, although the final product is obtained in higher amount with said process than with the process previously mentioned, anyway the total yield does not exceed 45%.

The Applicant has unexpectedly found a process for preparing terfenadine in higher yields which does not require many steps. The process for preparing the compound of formula I according to the present invention comprises a) reacting the isonipecotate of formula II':

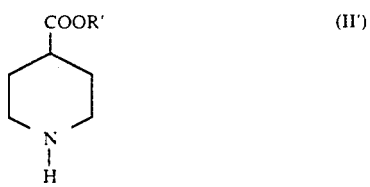

in which R' is a $C_1$-$C_5$ alkyl or an arylalkyl selected from benzyl, with 1-(alkylphenyl)-4-chloro-butanol IX:

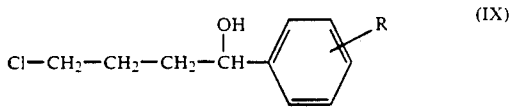

in which R' is a $C_1$-$C_5$ alkyl radical to obtain the compound of formula V':

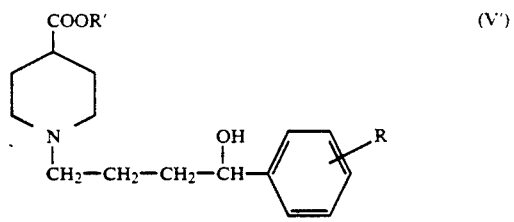

b) reacting the compound (V') with phenyl magnesium halide to obtain the compound of formula (I).

By using the process according to the present invention it is possible to obtain terfenadine in a lesser number of steps, in much higher yields: above 70%, and in very pure form.

The step (a) of the process according to the present invention is carried out by boiling under reflux in a reaction medium consisting of an organic solvent in the presence of an inorganic base.

The preferred solvent is acetonitrile, but dimethylformamide, dimethylacetamide, ethylacetate, dioxane tetrahydrofuran, acetone, methylethylketone, toluene or their mixture can be used.

The inorganic base used can be either a carbonate or bicarbonate of an alkaline or an earth metal, such as $Na_2CO_3$, $CaCO_3$, or $Li_2CO_3$.

The molar ratio of (II) to (IX) used in the reaction is stoichiometric.

The step b is conducted in an organic solvent at temperatures ranging from 40° to 50° C.

The preferred organic solvent for this reaction is tetrahydrofuran, but other solvents can be used such as ethylether, isopropylether, butylether and others.

The phenyl magnesium halide is preferably phenyl magnesium bromide, or phenyl magnesium chloride.

The molar ratio of V' to phenylmagnesium halide is stoichiometric.

The following example of the preparation of the compound of formula (I) is given by way of non limiting illustration of the present invention.

EXAMPLE 1

The following are fed into a flask fitted with a reflux condenser, a stirrer and a thermometer:
300 g (1.25 mol) of 1-(p-tert.butyl phenyl)-4-chlorobutanol
1 l of acetonitrile
160 g (1.02 mol) of ethyl-isonipecotate
200 g of potassium carbonate
and the mixture is heated under reflux for 24 hours.

The reaction mixture is then poured into a mixture of 5 l of water with 1 l of methylene chloride.

The mixture obtained is then stirred and the methylene chloride containing the product is separated and evaporated to dryness under vacuum.

The residue is treated with 500 ml of tetrahydrofuran and heated to 40°-50° C. until completely dissolved.

To this solution at 40° C., 1420 g are slowly added of a 25% solution of phenyl magnesium chloride in tetrahydrofuran, and on completion of the addition the mixture is heated to 50° C. for 5 hours.

The reaction mixture is then cooled to 20° C. and poured into 1 l of water, the mixture acidified with hydrochloric acid to acid pH and alkalified with a dilute caustic soda solution to basic pH in the presence of methylene chloride.

The organic phase is separated, dried with anhydrous sodium sulphate, filtered and then concentrated to dryness.

The residue is then crystallized from acetone to obtain 350 g (0.74 mol) of the required product (yield based on the ethyl isonipecotate initially charged = 73%), having the following characteristics.
Titre: 99.95%
M.P. 150°-152° C.

| Elementary Analysis for $C_{32}H_{41}NO_2$ M.W. = 471.69 | | | | |
| --- | --- | --- | --- | --- |
| | C(%) | H(%) | N(%) | O(%) |
| CALCULATED | 81.48 | 8.76 | 2.97 | 6.78 |
| FOUND | 81.42 | 8.71 | 2.94 | 6.78 |

I claim:

1. A process for preparing alpha-(alkylphenyl)-4-(hydroxydiphenylmethyl)1piperidine butanol of formula (I)

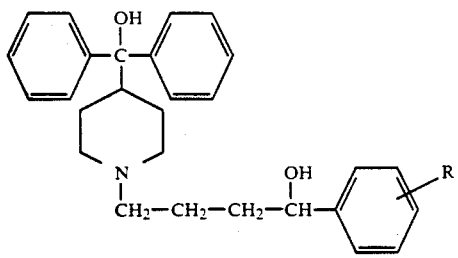

in which R is a $C_1-C_5$ alkyl, comprising:

a) reacting an alkyl isonipecotate of formula II

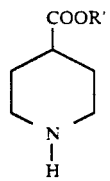

in which R' is a $C_1-C_5$ alkyl or benzyl, with 1-(alkylphenyl)-4-chloro-butanol IX:

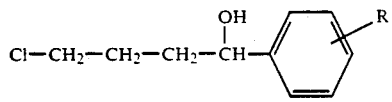

wherein R has the above mentioned meanings, to obtain the compound of formula V':

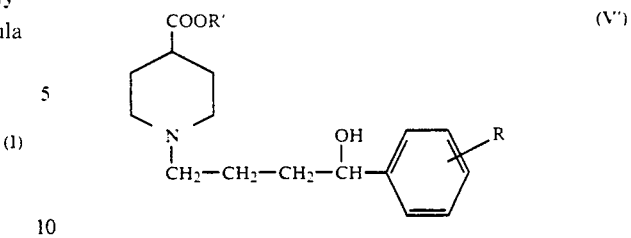

b) reacting the compound (V') with phenyl magnesium halide to obtain the compound of formula (I).

2. The process according to claim 1 wherein step a is conducted in an organic solvent at the boiling solvent temperature under reflux conditions, in the presence of an inorganic base.

3. The process according to claim 2 wherein the organic solvent is selected from the class consisting of acetonitrile, dioxane, dimethylacetamide, dimethylformamide, ethylacetate, tetrahydrofuran, acetone, methylethylketone, toluene or their mixture.

4. The process according to claim 2 wherein the organic base is selected from the class consisting of: carbonate or bicarbonate of an alkaline or an earth alkaline metal.

5. The process according to claim 1 wherein step a is carried out with a stochiometric molar ratio of the reactants.

6. The process according to claim 1 wherein in step b the phenylmagnesium halide is phenylmagnesium bromide or phenyl magnesium chloride.

7. The process according to claim 1 wherein step b is carried out in the presence of an organic solvent selected from the group consisting of tetrahydrofuran, ethylether, isopropylether, or butyl ether.

8. The process according to claim 1 wherein step b is carried out at temperatures ranging from 40° to 50° C.

9. The process according to claim 1 wherein step b is carried out with a stochiometric molar ratio of the reactants.